United States Patent [19]
Denmark

[11] Patent Number: 6,019,773
[45] Date of Patent: Feb. 1, 2000

[54] TONGUE CLEANER

[76] Inventor: Stanley J. Denmark, 330 E. 80 St., #2D, New York, N.Y. 10021

[21] Appl. No.: 09/246,980

[22] Filed: Feb. 8, 1999

[51] Int. Cl.$^7$ ..................................................... A61B 17/24
[52] U.S. Cl. ............................................................ 606/161
[58] Field of Search .................................... 606/160, 161, 606/162

[56] References Cited

U.S. PATENT DOCUMENTS

| | | | |
|---|---|---|---|
| 4,617,694 | 10/1986 | Bori | 15/160 |
| 4,831,676 | 5/1989 | Denmark | 15/104.93 |
| 5,792,159 | 8/1998 | Amin | 606/161 |
| 5,817,114 | 10/1998 | Anderson et al. | 606/161 |

*Primary Examiner*—Michael Buiz
*Assistant Examiner*—Vy Q. Bui

*Attorney, Agent, or Firm*—Bauer & Schaffer, LLP

[57] ABSTRACT

An improved dental prophylaxis device for cleansing the teeth of a user and massaging the gums of the user of a type having a pair of absorbent core members that are convexo-concave-shaped and have convex surfaces and which are saturated with dental cleansing material and which are flexible but capable of retaining their shape and which are enclosed in a spaced-apart disposition within a saturable covering layer that has a longitudinal center line and a variegated surface and a portion between the pair of absorbent core members that is flexible and indented and defines a lateral centerline. The improvement includes a pocket being disposed on the saturable outer covering layer for receiving the forefinger of a user and enabling the user to rub said improved prophylaxis device against the teeth of the user and the gums of the user using the pressure of only the forefinger of the user without dropping the improved prophylaxis device and without having to utilize more than one finger of at least one hand of the user.

9 Claims, 2 Drawing Sheets

Fig. 1
(PRIOR ART)
Fig. 2
(PRIOR ART)
Fig. 3
(PRIOR ART)
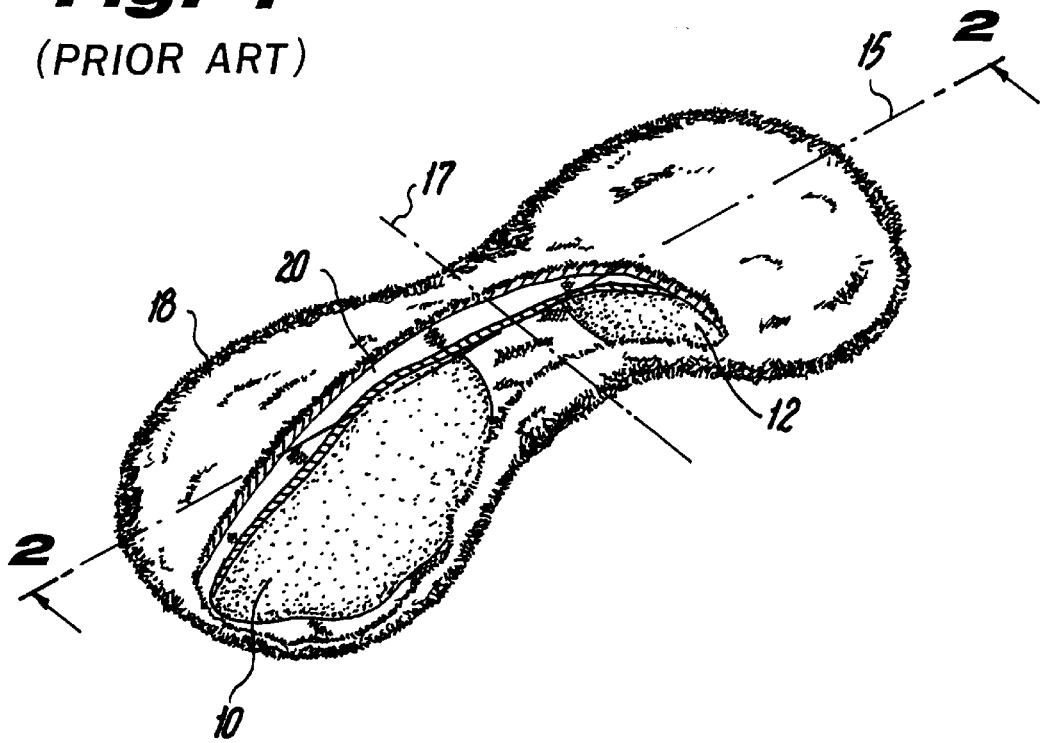
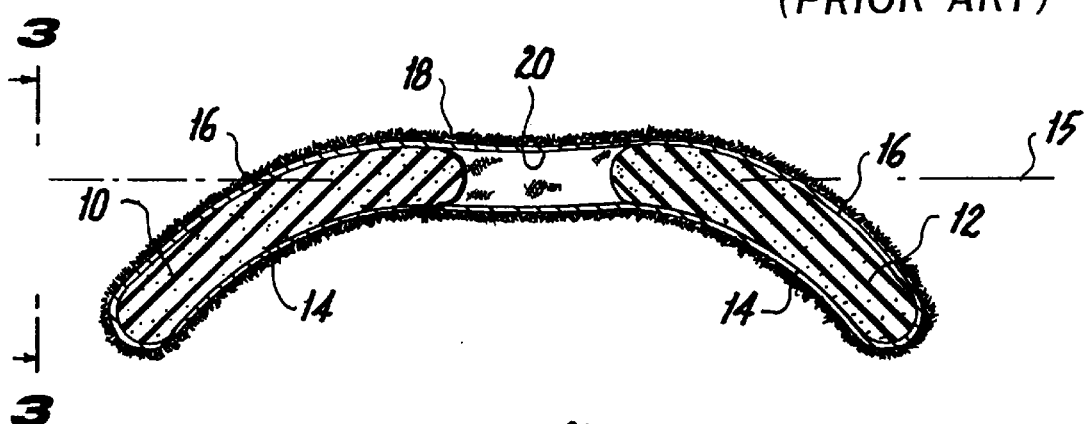
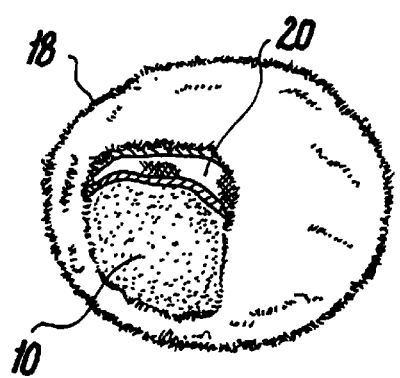

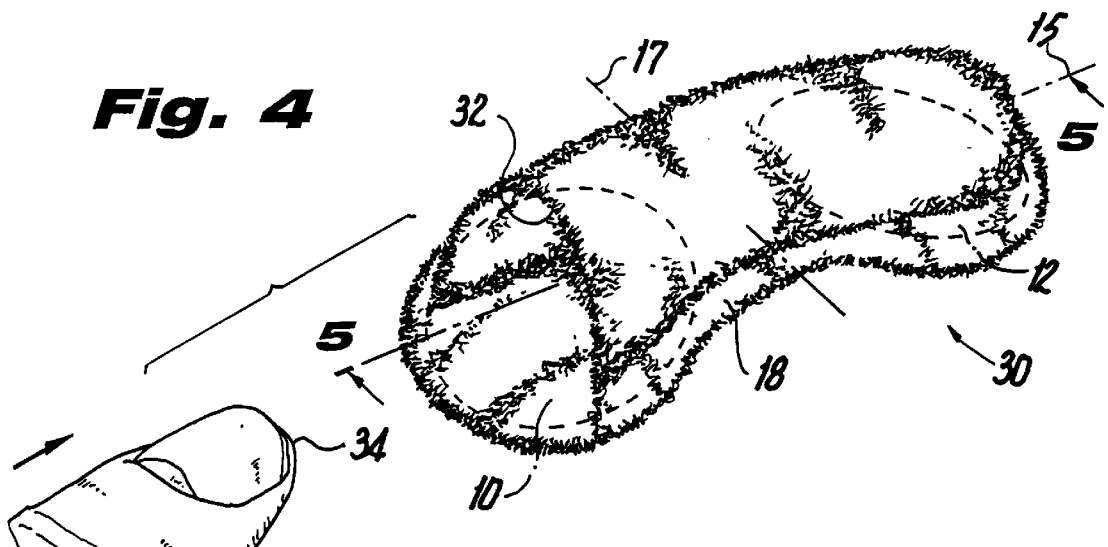
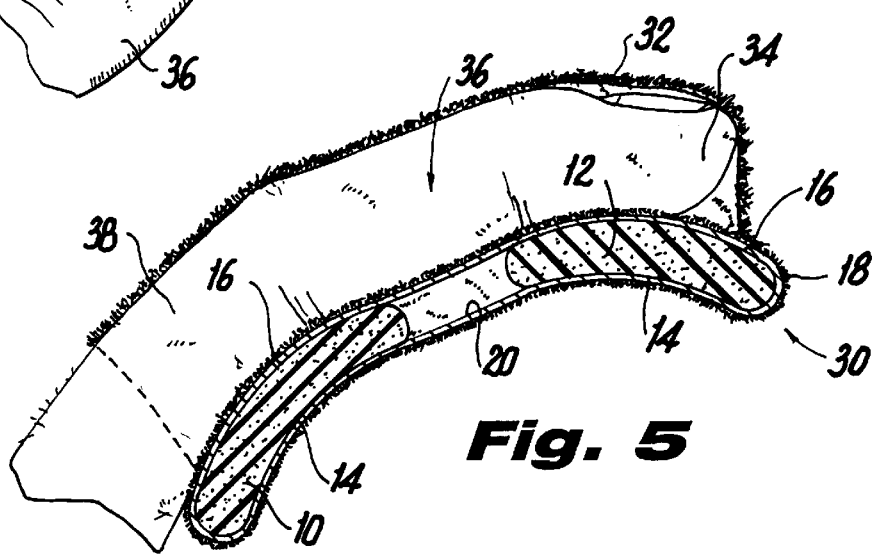
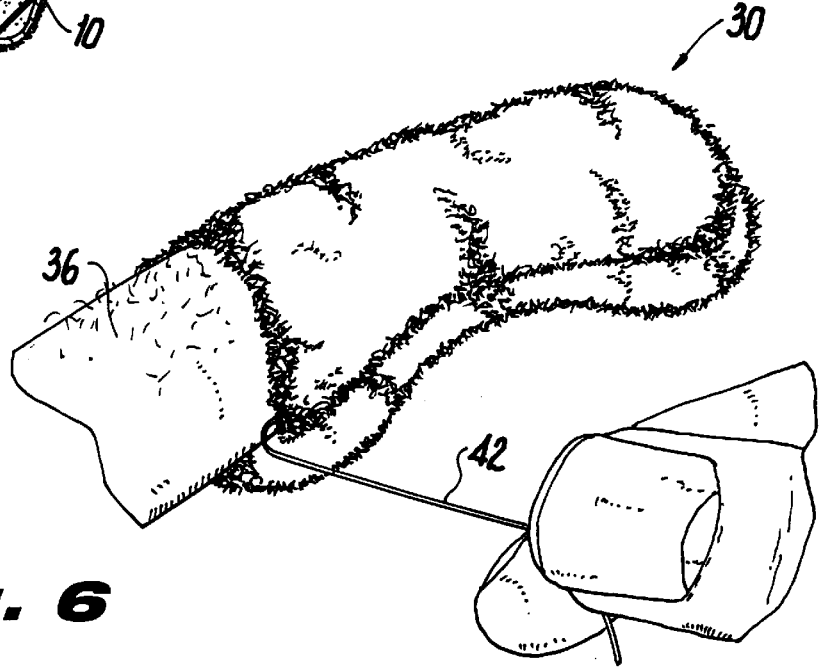

TONGUE CLEANER

BACKGROUND OF THE INVENTION

The present invention relates to an improved dental prophylaxis device. More particularly, the present invention relates to an improved dental prophylaxis device for cleaning the tongue and teeth, as well as massaging the gums.

Other than conventional brushes, a wide variety of dental prophylaxis devices for cleansing the teeth and massaging the gums as well as applying medication thereto to treat, for example, periodontal disease, are known. Many of these devices contain medication and/or dentifrice as an integral part thereof. However these devices as whole are ineffective at cleaning the tongue.

Numerous innovations for dental prophylaxis devices have been provided in the prior art. Even though these innovations may be suitable for the specific individual purposes to which they address, however, they differ from the present invention.

Examples of such devices are disclosed in U.S. Pat. Nos. 4,665,901; 4,617,694; 4,335,731; 3,675,264; 3,109,192; 2,999,260; 2,966,691; 2,112,184; and 2,763,885. These devices are generally attachable to one or more fingers for insertion into the mouth and manipulation over the teeth and gums.

Still further, a disposable surgical scrub sponge impregnated with detergent is disclosed in U.S. Pat. No. 3,369,419, and a method of producing a sponge impregnated with detergent is disclosed in U.S. Pat. No. 3,112,219, while U.S. Pat. No. 20,057,500 discloses a combination of waxes and polishes.

On the other hand, tooth and/or gum brushes, of a variety of configurations, and some of which have a self-contained supply of medication and/or dentifrice, are also known as may be seen from U.S. Pat. Nos. 4,399,582; 3,193,864; 2,807,820; British Pat. No. 2,129,675; and German Pat. No. 2,147,727.

The devices of the type described above are generally ill-suited to for use as a tongue cleaner because of their relatively hard comb or brush like structure that are abrasive to the soft, sensitive surfaces of the tongue. The non-brush prior art devices are cumbersome and therefore can not reach the rear or dorsal sections of the tongue where the majority of oral malodor originates. In addition, many of the prior art devices require the use of the entire hand and/or multiple finger of one or both hands to operate the same. Consequently, they are ineffective as a tongue cleaner as then can not be easily positioned within the mouth to reach all sections of the tongue especially the dorsal third of the same where the majority of oral malodor originates. Furthermore, the prior art devices are generally ineffective at getting into the pores, crevices formed by the furrows, taste buds and other papillae of the tongue and therefore can not thoroughly clean the same.

A prior art dental appliance device, of which the present invention is an improvement of, is taught by my U.S. Pat. No. 4,831,676, which is incorporated herein by reference.

Referring to FIGS. 1 and 2, the dental prophylaxis device as disclosed in my prior patent comprises a pair of absorbent core members 10 and 12, which are flexible, but capable of retaining their shape, and which are saturated completely with a liquid or semi-liquid (i.e. a gel or a cream) cleansing material which may also include an oral deodorant or even medication.

The pair of core members 10 and 12 may be made from suitably shaped natural sponge material or sponge-like material which may be made from synthetic, polymeric sponge-like materials, or semi-rigid synthetic polymeric foams, such as polyethylene, acrylic, polyester, polyamide, and polyurethane sponges, as well as semi-rigid foams and the like.

The pair of core members 10 and 12 are preferably coin-shaped i.e. generally circular, and are curved (in diametric section) to have concave and convex surfaces 14 and 16, respectively, thus allowing the prior art device to conform more readily to the shape of the teeth and gums.

The pair of core members 10 and 12 are enclosed in a spaced-apart disposition, within a saturable outer covering layer 18 having a longitudinal center line 15 and a variegated or rough portion and another portion between the pair of core members 10 and 12 that defines a lateral centerline 17 that is flexible and indented, so that when the prior art device is inserted in the mouth, the labile muscles in the center of the lips do not interfere with the movement of the prior art device over the teeth and gums.

The saturable outer covering layer 18 may be made out of any suitable textile material having a soft, but variegated or rough surface. Preferred materials are gauze pile or terry cloth, and the like.

A second and inner layer 20 of soft, strong covering material, which is coextensive in size with the saturable outer covering layer 18, is disposed between the pair of core members 10 and 12 and the saturable outer covering layer 18.

The second and inner layer 20 may be made from any soft, strong textile material, with gauze being a preferred material useful to make the same.

The prophylaxis device as disclosed in my prior patent may be manufactured and placed in sealed, sterile envelopes after it has been rendered sterile, so that it may be shipped for distribution and marketing ready for use. The exudate or exudates may be tasteful or tasteless. The anti-rough surface stimulates and aids in massaging the gums and cleansing the teeth.

Moreover, the device being bendable or flexible is capable of applying massaging action and cleansing action to both the inside and outside gum and teeth surfaces, conforming well thereto. In addition, after use it may be thrown away, thus lessening the possibility of reinfecting the gums and teeth which reusable brushes often tend to do.

In use, the device is placed flat against the upper or lower gums and teeth, by use of either the fingers of both hands or the fingers of either hand to apply pressure and to prevent dropping thereof, and pressed to release the liquid or cream contained in the flexible covers to allow it to exude outwardly from the cores, through the covering layer or layers, and thence onto the teeth and gums. The user, by use of either the fingers of both hands or the fingers of either hand to provide pressure and to prevent dropping, then moves the device across the surfaces of the teeth and gums, thus achieving gum massage, dental cleaning, and mouth deodorizing where a deodorant is included.

It is apparent that numerous innovations for dental prophylaxis devices have been provided in the prior art. Furthermore, even though these innovations may be suitable for the specific individual purposes to which they address, however, they would not be suitable for the purposes of the present invention as heretofore described.

Thus, there still exists a need for an improved device of the above-described type which enables the user to rub the device against tongue, teeth and gums using the pressure of only the forefinger without dropping the device and without having to hold the device with either fingers of both hands, or the fingers of the right or left hand to prevent dropping and to rub the oral tissues.

It is therefore, an object of the present invention is to provide an improved dental prophylaxis device that avoids the disadvantages of the prior art.

It is therefore, an object of the present invention to provide an improved dental prophylaxis device for cleaning the tongue and teeth, as well as massaging the gums.

It is another object of the present invention to provide an improved dental prophylaxis device that effectively cleans the all portions of the tongue including the anterior and posterior sections of the same.

It is yet another object of the present invention to provide an improved dental prophylaxis device that effectively cleanse the pores and crevices formed by the furrows, taste buds and other papillae of the tongue.

It is still another object of the present invention is to provide an improved dental prophylaxis device that is simple to make and use.

It is a further object of the present invention is to provide an improved dental prophylaxis device that is inexpensive to manufacture.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

SUMMARY OF THE INVENTION

The present invention provides an improved dental prophylaxis device for cleansing the tongue, as well as the teeth and gums of the user of a type having a pair of absorbent core members that are convex-concave-shaped and have convex surfaces and which are saturated with dental cleansing material and which are flexible but capable of retaining their shape and which are enclosed in a spaced-apart disposition within a saturable covering layer that has a longitudinal center line and a variegated surface and a portion between the pair of absorbent core members that is flexible and indented and defines a lateral centerline. The improvement includes a pocket being disposed on the saturable outer covering layer for receiving the forefinger of a user and enabling the user to rub the improved prophylaxis device against the teeth of the user and the gums of the user using the pressure of only the forefinger of the user without dropping the improved prophylaxis device and without having to utilize more than one finger of at least one hand of the user.

BRIEF DESCRIPTION OF THE DRAWING

FIG. 1 is a diagrammatic perspective view, in partial section, of the prior art dental prophylaxis device taught by my U.S. Pat. No. 4,831,676;

FIG. 2 is a diagrammatic cross sectional view taken along line 2—2 in FIG. 1;

FIG. 3 is a diagrammatic end elevational view, in partial section, taken generally in the direction of arrow 3 in FIGS. 1 and 2;

FIG. 4 is a diagrammatic perspective view of the present invention; and

FIG. 5 is a diagrammatic cross sectional view taken along line 4—4 in FIG. 4.

FIG. 6 is a diagrammatic perspective view of the present invention with a lenght of dental floss.

DETAILED DESCRIPTION OF THE INVENTION

Referring now to the figures, in which like numerals indicate like parts, and particularly to FIGS. 4 and 5, the improved dental prophylaxis device of the present for cleaning the tongue, cleaning the teeth and massaging the gums of the user is generally depicted by the numeral 30.

The improvement of the improved dental prophylaxis device 30 comprises a pocket 32 being disposed on the saturable outer covering layer 18 for receiving the forefinger 36 of a user and enabling the user to rub the improved prophylaxis device 39 against the entire surface of the tongue including the anterior and posterior sections of the same, while at the same time cleaning the teeth and massaging the gums. The configuration of the covering layer 18 enables the user to clean the tongue by using only the pressure the forefinger 36. The configuration of the covering layer 18 further prevents the dropping of the improved prophylaxis device 30 and avoids the need to use more than one finger while operating the device. This enables the user to easily position the improved phophylxis device so as to clean all portions of the tongue including the anterior and posterior (dorsal) sections of the same.

The improvement of the improved dental prophylaxis device 30 further comprises the pocket 32 being disposed along the longitudinal centerline 15 of the saturable outer covering layer 18.

The improvement of the improved dental prophylaxis device 30 further comprises the pocket 32 being disposed on the saturable outer covering layer 18, above the convex surface 16 of one core member of the pair of core members 10 and 12.

The improvement of the improved dental prophylaxis device 30 further comprises the pocket 32 extending longitudinally from the lateral centerline 17 of the saturable outer covering layer 18, along the saturable outer covering layer 18, above one, core member of the pair of core members 10 and 12.

The improvement of the improved dental prophylaxis device 30 further comprises the pocket 32 extending along the longitudinal centerline 15 of the saturable outer covering layer 18 from the lateral centerline 17 of the saturable outer covering layer 18 where it opens, along the saturable outer covering layer 18, above the convex 16 surface of one core member of the pair of core members 10 and 12, which allows the tip 34 of the forefinger 36 of the user to be releasably captured in the pocket 32, with the remainder 38 of the forefinger 36 of the user extending longitudinally along the saturable outer covering layer 18, above the other core member of the pair of core members 10 and 12, and flexing as necessary the lateral centerline 17 of the saturable outer covering layer 18.

The improvement of the improved dental prophylaxis device 30 further comprises the pocket 32 being made of the same material as the saturable outer covering layer 18.

The improvement of the improved dental prophylaxis device 30 further comprises the pocket 32 being made of terry cloth. The terry cloth material is soft and gentle so as not to damage the sensitive structure of the tongue while at the same time is effective at cleaning between the furrows, taste buds and other papillae of the tongue. Thus when the terry cloth material is impregnated with either odor defeating liquids, and/or liquid medications, and rubbed along the surface of the tongue it will easily break down the bacteria (e.g. sulphur-type) that are the origin of oral malodor (halitosis).

The improved dental prophylaxis device may further include a length of dental floss 42 attached to one end of to the outer covering layer 18 as shown. The dental floss may be wrapped around the user's finger to help assist the user in holding the prophylaxis device or it may be used to floss the interproximal areas between the teeth. In this way the user can use the dental floss to help secure the device to his finger and then use the dental floss to clean the interproximal areas between the teeth. In any event, the dental floss 42 should preferably be about seven to about eight inches in length.

It will be understood that each of the elements described above, or two or more together, may also find a useful application in other types of constructions differing from the types described above.

While the invention has been illustrated and described as embodied in an improved dental prophylaxis device for cleaning the tongue, teeth and massaging the gums of a user, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An improved dental prophylaxis device for cleansing the tongue and teeth of a user and massaging the gums of the user of a type having a pair of absorbent core members that are convexo-convex-shaped and have convex surfaces and which are saturated with dental cleansing material and which are flexible but capable of retaining their shape and which are enclosed in a spaced-apart disposition within a saturable covering layer that has a longitudinal center line and a variegated surface and a portion between the pair of absorbent core members that is flexible and indented and defines a lateral centerline, the improvement comprising a pocket being disposed on the saturable outer covering layer for receiving the forefinger of a user and enabling the user to rub said improved prophylaxis device against the teeth of the user and the gums of the user using the pressure of only the forefinger of the user without dropping said improved prophylaxis device and without having to utilize more than one finger of at least one hand of the user.

2. The improvement as defined in claim 1, wherein the improvement further comprises said pocket being disposed along the longitudinal centerline of the saturable outer covering layer.

3. The improvement as defined in claim 1, wherein the improvement further comprises said pocket being disposed on the saturable outer covering layer, above the convex surface of one core member of the pair of core members.

4. The improvement as defined in claim 1, wherein the improvement further comprises said pocket extending longitudinally from the lateral centerline of the saturable outer covering layer, along the saturable outer covering layer, above one core member of the pair of core members.

5. The improvement as defined in claim 1, wherein the improvement further comprises said pocket extending along the longitudinal centerline of the saturable outer covering layer from the lateral centerline of the saturable outer covering layer where it opens, along the saturable outer covering layer, above the convex surface of one core member of the pair of core members, which allows the tip of the forefinger of the user to be releasably captured in the pocket, with the remainder of the forefinger of the user extending longitudinally along the saturable outer covering layer, above the other core member of the pair of core members, and flexing as necessary the lateral centerline of the saturable outer covering layer.

6. The improvement as defined in claim 1, wherein the improvement further comprises said pocket being made of the same material as the saturable outer covering layer.

7. The improvement as defined in claim 1, wherein the improvement further comprises said pocket being made of terry cloth.

8. The improvement as defined in claim 1, wherein the improvement further comprises a length of dental floss attached to said outer covering layer.

9. The improvement as defined in claim 8, wherein said length of dental floss is about seven to about eight inches.

* * * * *